(12) United States Patent
Vadgama et al.

(10) Patent No.: US 6,706,532 B2
(45) Date of Patent: Mar. 16, 2004

(54) MEMBRANE FOR CHEMICAL AND BIOSENSORS

(75) Inventors: Pankaj Maganlal Vadgama, Manchester (GB); Subrayal Medapati Reddy, Manchester (GB); Marika S.K. Kyrolainen, Lund (SE)

(73) Assignee: The Victoria University of Manchester, Manchester (GB)

( * ) Notice: Subject to any disclaimer, the term of this patent is extended or adjusted under 35 U.S.C. 154(b) by 213 days.

(21) Appl. No.: 09/068,333
(22) PCT Filed: Nov. 7, 1996
(86) PCT No.: PCT/GB96/02747
 § 371 (c)(1),
 (2), (4) Date: Oct. 29, 1998
(87) PCT Pub. No.: WO97/17607
 PCT Pub. Date: May 15, 1997

(65) Prior Publication Data
 US 2002/0025580 A1 Feb. 28, 2002

(30) Foreign Application Priority Data
 Nov. 8, 1995 (GB) .............................................. 9522842
 Aug. 30, 1996 (GB) .............................................. 9618153

(51) Int. Cl.$^7$ .......................... C12Q 1/00; G01N 33/48
(52) U.S. Cl. ...................... 436/149; 436/166; 436/169; 422/61; 204/400; 204/402; 204/403.05
(58) Field of Search ................................ 436/149, 164, 436/166, 169; 204/403, 400, 402, 403.01, 403.05; 435/4; 422/82.01, 61, 58

(56) References Cited

U.S. PATENT DOCUMENTS

| 4,919,767 A | * | 4/1990 | Vadgama et al. ............ 205/778 |
| 5,240,571 A | * | 8/1993 | Heineman et al. ......... 205/777.5 |
| 5,264,106 A | * | 11/1993 | McAleer et al. .......... 205/777.5 |
| 5,326,449 A | * | 7/1994 | Cunningham ................ 204/403 |
| 5,401,377 A | * | 3/1995 | Shieh et al. ................. 204/418 |
| 5,746,898 A | * | 5/1998 | Preidel ......................... 204/403 |
| 5,837,446 A | * | 11/1998 | Cozzette et al. ................ 435/6 |

FOREIGN PATENT DOCUMENTS

| EP | A 0 138 150 | 4/1985 |
| WO | WO A 94 02584 | 2/1994 |
| WO | 9520050 | * 7/1995 |
| WO | WO A 96 15223 | 5/1996 |

OTHER PUBLICATIONS

J. Baro–Roma et al; "Construction and development of ion–selective electrodes responsive to anionic surfactants"; Sensors and Actuators B, 15–16 (1993) pp. 179–183; XP009004591.

* cited by examiner

Primary Examiner—Lyle A. Alexander
(74) Attorney, Agent, or Firm—Nixon and Vanderhye

(57) ABSTRACT

Aqueous membrane permeable by mass transport to a charged and uncharged species of interest, comprising a synthetic polymeric material and a surface active agent which is miscible with the synthetic polymer. The surface active agent is distributed throughout the membrane and is present in an amount such as to provide for the permeability of the membrane to the species of interest.

44 Claims, 14 Drawing Sheets

Permeability of PVC modified with BEP (100 μl; 161%(w/w)) in a succinate buffer (pH2.9).

Measure of degree of leaching with time when surfactant modified PVC membranes are bathed in distilled water.

● PVC(Tw,177%(w/w)) ■ PVC(Tr,180%(w/w))

MEMBRANE FOR CHEMICAL AND BIOSENSORS

The present invention relates to a membrane which is intended particularly, but not exclusively, for use in a sensor, to a sensor incorporating such a membrane, and to a detection method utilising the membrane. The membranes of the invention are intended most particularly (but again not exclusively) for use in chemical and biosensors, e.g. for determining the amount of lactate in whole blood, (this being a measure of the oxygenated state of tissue).

BACKGROUND OF THE INVENTION

Biosensors are used for detecting the presence and/or amount of a selected component in a sample, e.g. blood. It is well known that biosensors comprise a combined detection arrangement of a biolayer such as an enzyme and a transducer. Certain types of biosensors have a membrane structure which comprises one or more membranes and which (in use of the biosensor) separates the detection arrangement from the sample being analysed. The membrane structure may contain a biological component (e.g. an enzyme) but usually separates the biological component from the sample. In the case of an enzyme there is a reaction with the species of interest to produce a product which is detected by the transducer; this gives one type of arrangement for "indirect" determination of the species of interest.

The membrane structure of the biosensor will generally include an outer membrane of a synthetic polymeric material which has been modified to produce a membrane which is permeable to the species of interest (or more permeable than a similar membrane produced from polymeric material which has not been modified). If the biosensor is to be used for operation in whole blood then the outer membrane (of the membrane structure) which comes into contact with the blood has to meet high demands on biocompatibility since sample pre-treatment preferably does not take place. The membrane surface will be a target for plasma proteins which will begin to adsorb rapidly after the initial contact with blood. Initial protein adsorption will be followed by complement activation, adhesion of cells and cell components and fibrin clot formation.

Operation in whole blood also puts demands on the linear range of the sensor which has to be much wider when there is no dilution of the sample prior to analysis.

DESCRIPTION OF THE INVENTION

According to a first aspect of the present invention there is provided a membrane comprised of a synthetic polymeric material incorporating a surface active agent.

By "surface active agent" we also mean "surfactants" and the terms may be used interchangeably.

The invention has been based on our finding that the incorporation of a surface active agent in a synthetic polymeric material renders membranes, produced from that material permeable (or more permeable) by mass transport to a species of interest whilst providing membranes which have good blood compatibility and which may be used to provide a response—linearising diffusion barrier. This is particularly the case for enzymes which have a reaction with the species of interest which has a rate that is not linear with respect to substrate concentrations when these are high (typically well above the enzyme Michaeli's constant).

The membranes may be rendered permeable to uncharged species or to charged species and may therefore be used in biosensors for determining the presence and/or amount of such charged species, e.g. the concentration of lactate present in a sample.

Membranes in accordance with the invention have the significant advantage of being blood compatible and may therefore be used in chemical sensors and biosensors for determining the amount of a species in whole blood. The membranes are thus particularly suitable for use in biosensors for determining the amount of lactate in whole blood. The membranes of the invention may however be used for other purposes, e.g. dialysis and as permeable covering layers on other enzyme and even non-enzyme electrodes. Moreover the membranes have utility in sensors for determining uncharged species, e.g. glucose and in chemical sensors which have no biological component.

It is a further advantage of the membranes of the invention that they provide a linearising diffusion barrier for the species of interest, i.e. the amount of the species present in a sample which is able to diffuse across the barrier is proportional to the amount of that species in the sample, but the concentration achieved after the barrier is crossed is thereby lowered and within the range for which the chemical or biosensor has a linear signal output.

Preferably the synthetic polymeric material is poly (vinylchloride). Preferably the poly(vinylchloride) will have a molecular weight (Mw) in the range 80,000 to 250,000, more preferably 150,000 to 250,000, e.g. about 200,000.

The amount of the surface active agent present in the membrane is generally at least 1% by weight of the synthetic polymer, e.g. more preferably at least 2%, even more preferably at least 3% on the same basis. Generally the amount of surface active agent is less than 250% by weight of the synthetic polymer. If the membrane is to be used in a sensor as a linearising diffusion barrier then the amount of surface active agent will depend on the intended use of the sensor. For some applications (e.g. use of the sensor under continuous flow conditions) it may be desirable for the amount of surface active agent to be at least 50% by weight of the synthetic polymer. For other applications the amount of surface active agent may be less than 50% (w/w) of the synthetic polymer, e.g. less than 30% or even less than 20% on the same basis. For dialysis membrane function, high mass transport (permeability) is required and higher amounts of surface active agent are demanded, typically in the range 100% to 200% (more preferably 150% to 200%) (w/w) of the synthetic polymer.

The surface active agent is preferably a non-ionic surface active agent. Such non-ionic surface active agents are particularly useful for avoiding specific ionic interactions with diffusing solute. Alternatively the surface active agent may be a cationic or anionic surfactant.

A variety of non-ionic surface active agents may be used. Surface active agents which are useful in the present invention include compounds comprised of or incorporating polyoxyalkylene residues. The alkylene oxide may for example be ethylene oxide and/or propylene oxide. Examples of such surface active agents include compounds of the formula (I)

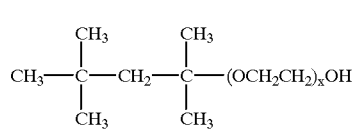

(I)

Typically the molecular weight of compound (I) will be in the range 500 to 800, e.g. from 600 to 700. A particularly suitable product of the formula (I) has a molecular weight of about 648 and is available under the name Triton X-100.

Further examples of surface active agents comprising poly(alkylene oxide) residues are block copolymers of ethylene oxide and propylene oxide. Suitable examples of such copolymers for use as surfactants have a molecular weight of 5000 to 10000, more preferably 7000 to 10000.

The block copolymer may be of the following general formula (I).

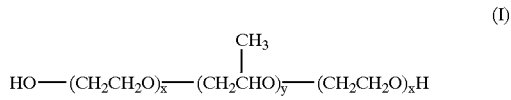

(I)

The block copolymer of ethylene oxide and propylene oxide may for preference have an ethylene oxide content of at least 75%, preferably about 80%, by weight of the surfactant.

Examples of preferred surfactants comprised of block copolymers of ethylene oxide and propylene oxide are available under the name PLURONIC. A particularly suitable example of such a product is available under the name Pluronic F-68 and has a molecular weight of about 8400.

If the surface active agent comprises a block copolymer of ethylene oxide and propylene oxide then it (i.e. the surface active agent) may comprise, for example, 4.5 to 100% by weight of the synthetic polymeric material, e.g. 6% to 100%, more preferably 10% to 90%, even more preferably 40% to 70%, and even more preferably 50% to 60% by weight on the same basis.

A further surface active agent which may be used is L-α-phosphatidyl choline dipalmitoyl ($C_{40}H_{80}NO_8P$) ($M_w=$ 734). This surface active agent occurs naturally as a pulmonary surfactant and has advantages from the point of view of biocompatibility. The inclusion of surfactants has generally led to improved haemocompatability in comparison with non-surfactant PVC membranes.

It is also possible to use analogues of surface active agents and such analogues are to be understood to be covered by the terms surface active agent as used herein. A particularly preferred analogue is bis(2-ethylhexyl) hydrogen phosphate which is of the formula

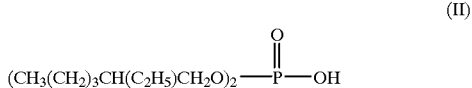

(II)

The above compound is referred to herein as BEP.

An important feature of a membrane comprised to PVC incorporating BEHHP is that membrane permeability can be made to be dependent on both buffer composition and pH. At pH 7 in either phosphate or carboxylic acid based buffers the PVC (BEHHP) membrane exhibits high permeability characteristics similar to those observed for PVC modified with either Tween 80 or Triton X-100. However, when interfaced with carboxylic acid based buffers (e.g. succinate buffer), at a pH where the acid buffer is predominantly in the neutral form (i.e. below it's pKa value), the PVC (BEHHP) will tend to switch to a low permeability state. PVC (BEHHP) could therefore be useful as a pH sensitive solute gating membrane.

Preferred membranes for use in a lactate sensor (referring to lactate determination in undiluted whole blood) comprise polyvinylchloride incorporating 10 to 45% (e.g. 18% to 45%) (w/w) of the non-ionic surface active agent Triton X-100 or 4.5–100% (w/w) of Pluronic F-68 or 1–3% (w/w) of L-α-phosphatidyl choline dipalmitoyl, the percentages being based on the weight of the poly(vinyl chloride). These values are particularly preferred for sensors which have an inner selective membrane (see later).

If the membrane is to be used for dialysis, the amount of surface active agent is preferably 150% to 200% (w/w/).

The membranes will typically have a thickness of 0.1 to 200 microns.

Membranes in accordance with the invention may be produced by conventional casting techniques. Alternatively the membrane may be produced by a "spin coating" technique in which a solution of the polymer in a volatile solvent is applied to a flat support surface which is then rotated (usually about a vertical axis) at a speed which causes the solution to be evenly distributed on the support and the solvent to be evaporated so as to produce a thin polymeric membrane of uniform thickness. The spin coating procedure allows membranes having a uniform thickness of 2 to 10 (e.g. 4 to 6) microns to be produced very quickly, e.g. from ten seconds to two minutes. The thickness of the membranes produced by the spin coating technique may also be readily controlled. The solution from which the membrane is formed by spin coating will generally have a concentration of 1 to 15% by weight, e.g. 2 to 10% by weight. To form the membrane, the polymer solution is applied on the axis about which the support is to be spun. Rotational speeds of 250 to 1500 rpm will generally be suitable. The support will generally be spun for up to two minutes, e.g. 90 seconds, to produce the desired membrane. A suitable apparatus for producing membranes by spin coating is a Photoresist Spinner as used for producing layers of photoresist materials. In all cases, a continuous membrane is produced in which the miscible surface active agent is distributed.

According to a second aspect of the present invention there is provided a sensor device comprising detecting means for detecting the amount of a species of interest in a sample and a membrane in accordance with the first aspect of the invention providing both a barrier function and a biocompatible interface function between the detecting means and the sample.

According to a third aspect of the present invention there is provided a method of determining the amount of a selected component in a sample the method comprising using a sensor device which incorporates means for detecting the amount of the component in a sample and a membrane in accordance with the first aspect of the invention, said membrane being located in contact with the sample and providing both a barrier function and a biocompatible interface function between the sample and the detection means.

The sensor device of the second aspect of the invention is preferably a biosensor but may be another form of sensor device.

The detecting system preferably comprises an electrochemical electrode system but may alternatively be in some other form such as a spectophotometric or optical system where physical contact with the sample is required. Where an electrochemical electrode system is used, it is preferably of the non-potentiometric type, examples of which include amperometric, galvanic, photo-galvanic and coulometric types. Most preferably the sensor device is a biosensor in which the detecting means comprises an amperometric electrode.

The method of the third aspect of the invention is particularly suitable for the determination of lactate in whole blood using an electrode detection system. In such a method, the lactate may be detected indirectly. Thus, for example, after diffusion through the membrane the lactate may interact with an enzyme on the electrode side of the membrane such that the interaction results in the production or consumption of a species which can be directly detected electrochemically. The enzyme may be immobilised in a layer provided between the membrane and the electrode. This layer may, for example, comprise the enzyme cross-linked with bovine serum albumin in a glutaraldehyde matrix. The enzyme may be entrapped in the membrane which may directly contact the sample or have an additional membrane containing surface active agent interposed between the enzyme containing membrane and sample.

The enzyme may, for example, be one which leads to the production of hydrogen peroxide which may then be detected. A suitable enzyme is an oxidase, e.g. lactate oxidase.

The enzyme layer may, if desired, incorporate catalase.

In addition to being permeable to lactate, the membrane of the invention may additionally be permeable to other species which could be interferents in the analysis of a particular sample using an enzyme electrode. In the case of blood, electroactive interferents include ascorbate, urate and acetaminophen (paracetamol), all of which will diffuse through the membrane of the invention. Sensors in accordance with the invention will therefore generally additionally include a further membrane (between the enzyme and the electrode) to provide selectivity against the interferents. Most preferably such a selective membrane is comprised of a sulphonated poly(ether ether sulphone)/(poly(ether sulphone) polymer (SPEES-PES) or cellulose acetate. Both without such a selective membrane or a selective biolayer (e.g. enzyme), direct electrochemical or other detection of electrode-active species is possible without external electrode fouling.

The sensor may be employed under continuous flow conditions, i.e. the sample to be analysed is supplied as a continuous flow to the sensor.

This method is particularly applicable to the determination of lactate in whole blood using a sensor device in which the detecting means comprises an enzyme electrode system of the type disclosed above, e.g. lactate oxide immobilised in a glutaraldehyde matrix. In monitoring the amount of lactate in whole blood under continuous flow conditions the blood may be treated with an anti-coagulation agent and then passed through a flow-through measurement cell. The necessary flow may be provided by a peristaltic pump.

Conveniently, the blood to be sampled is passed in one direction along the inner lumen of a double lumen catheter whilst the anti-coagulation agent is passed in the opposite direction through the outer lumen for admixture with the blood as it enters the inner lumen.

The anti-coagulant should be present at a sufficient concentration to prevent coagulation. Preferably the anti-coagulation agent is heparin.

The flow rate of the anti-coagulation agent may be at least equal to that of the blood. Thus, for example, the blood may provide 20 to 50%, eg. 30% of the total volume of mixed blood and anti-coagulant.

In use of a device in accordance with the second aspect of the invention it is possible (and may possibly be desirable) that there will be some continuous leakage of surface active agent from the membrane surface in contact with the sample. In fact, continuous loss of surface active agent and its surface replacement may eliminate fouling by resulting in a self-regenerating and therefore self-cleaning surface. In fact, the degree of fouling observed microscopically associated with devices incorporating membranes in accordance with the first aspect of the present invention is amongst the lowest for any known membrane or polymer material that has been exposed to blood.

It may therefore be desirable to provide an additional source of surface agent to replenish that lost from the membrane. Thus for example, a reservoir of surface active agent may be provided around an extended area of the membrane (i.e. on one or both sides of the membrane extended beyond the detection surface of the sensor). Alternatively a source of surface active agent may be pre-loaded into the extended side of the membrane remote from the detection means and from the part of the membrane exposed to sample and serve to supply surface active agent through the membrane to replace that lost across the part of the membrane in contact with the sample.

BRIEF DESCRIPTION OF THE DRAWINGS

The invention is illustrated by the following non-limiting Examples and accompanying FIGS. 1 to 9 and 11 to 14 which illustrate the results of the Examples, and FIG. 10 which illustrates a catheter used in the procedures of Examples 8 to 11.

Unless stated otherwise, all percentages in the Examples are w/w.

EXAMPLE 1

(i) PVC Membranes

A volume of 5 ml of tetrahydrofuran (THF) was mixed with 10 $\mu$l of Triton X-100 (ex Aldrich). To this mixture was added 0.06 g of PVC (molecular weight 200,000; ex BDH) and the polymer was allowed to dissolve overnight. The resulting polymer solution was poured into a glass Petri dish (diameter=10 cm) which was then covered with a glass lid and allowed to stand at room temperature for two days in order to allow for slow solvent operation.

The resultant membrane comprised 18% w/w of TRITON X-100.

The above procedure was repeated using amounts of TRITON X-100 of 15 $\mu$l, 25 $\mu$l and 50 $\mu$l so as to produce membrane containing 27% w/w, 45% w/w and 90% w/w TRITON X-100 respectively.

(ii) Enzyme Laminate

A solution containing 300 mg ml$^{-1}$ bovine serum albumin (ex Sigma) and 15 mg ml$^{-1}$ lactate oxidase, LOD, from Pediococcus Species (40 U mg$^{-1}$; ex Sigma) was prepared. A cross-linked enzyme layer was obtained by mixing 6 $\mu$l of the enzyme solution with 3 $\mu$l of a 0.5% (v/v) glutaraldehyde solution on a dialysis membrane. A further dialysis membrane was quickly positioned on top of the enzyme layer and the laminate pressed together using microscope slides. After removal of the glass slides, the laminate was air dried for a few minutes and washed with buffer to remove any excess glutaraldehyde.

Four laminate membranes were produced. Each such laminate membrane comprised one of the four PVC membranes prepared as described under (i) and an enzyme layer (prepared as described under (ii)). The laminate membranes were evaluated in a sensor arrangement to determine the response obtained to various concentrations of lactate. The sensor used comprised a Rank electrode (ex Rank Brothers)

consisting of a platinum working electrode polarised at +650 mV vs. Ag/AgCl for the detection of $H_2O_2$ and a silver cathode acting as a pseudo reference electrode. Signal responses were recorded with an x-t chart recorder.

Figure 1:
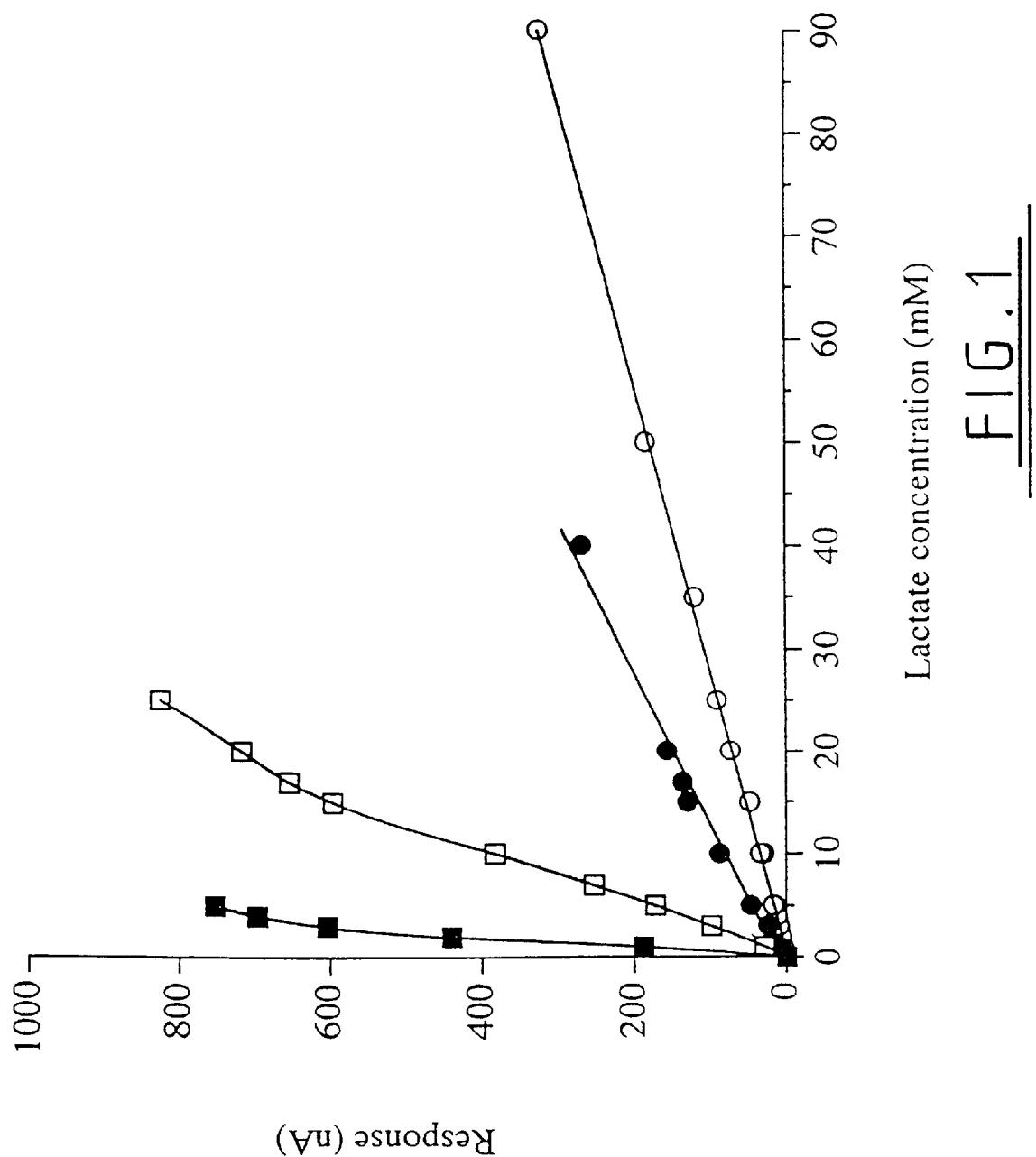

The results for the four composite membranes are shown in FIG. 1 in which the various PVC membranes are represented by the following symbols ■ 90% w/w TRITON X-100
□ 45% w/w TRITON X-100
● 27% w/w TRITON X-100
○ 18% w/w TRITON X-100.

It will be seen from FIG. 1 that all membranes were permeable to lactate and that in all cases the response was substantially linear. The lactate permeability decreased with decreasing amount of Triton X-100 in the PVC membrane resulting in an increased linear range for the lactate sensor. The least permeable membranes gave a linearity beyond that needed for clinical measurements. However, this characteristic might well be of use in other applications such as the food industry.

EXAMPLE 2

This example demonstrates the properties of a composite membrane comprised of (i) a PVC membrane containing 23% w/w Triton X-100 (prepared as described in Example 1);

(ii) an enzyme layer (prepared as described in Example 1); and (iii) a SPEES/PES layer (prepared as described below)

in the determination of lactate. The SPEES/PES layer was prepared according to a previous method (S. Ghosh, PhD Thesis, University of Manchester 1994) modified as follows. An amount of 0.1 g of SPEES/PES (sulphonation ratio=5; ex ICI) was dissolved in a mixture of 3.75 ml N,N-dimethylformamide and 1.25 ml 2-methoxy ethanol. The polymer was left to dissolve overnight and then a membrane was cast using a glass Petri dish. Due to the low volatility of the solvents used, the dish was left uncovered at room temperature and a period of four days was allowed before the membrane was used.

Figure 2:
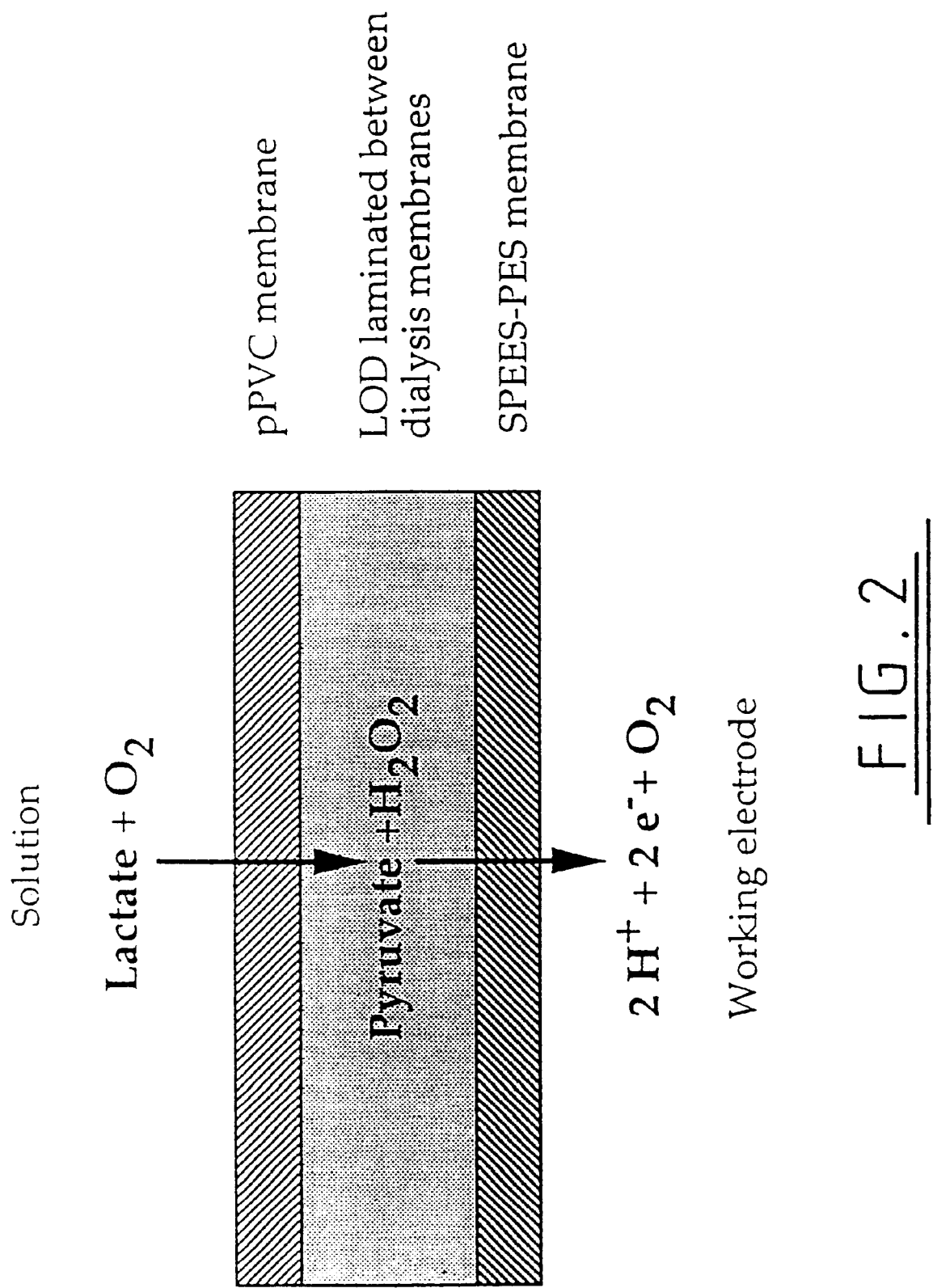

The composite membrane which comprised layers (i), (ii) and (iii) is diagrammatically illustrated in FIG. 2. This composite membrane was incorporated in the Rank electrode as described in Example 1 and tested for its properties for determining lactate in solution, both before exposure to whole blood and after the exposure (for a total of about one hour) to whole blood described in Example 3 below. The results are shown in FIG. 3 which shows calibration of the electrode before, (□)y=23.329x+0.129, and after, (■)y=22.414x+0.529, exposure to blood.

Figure 3:
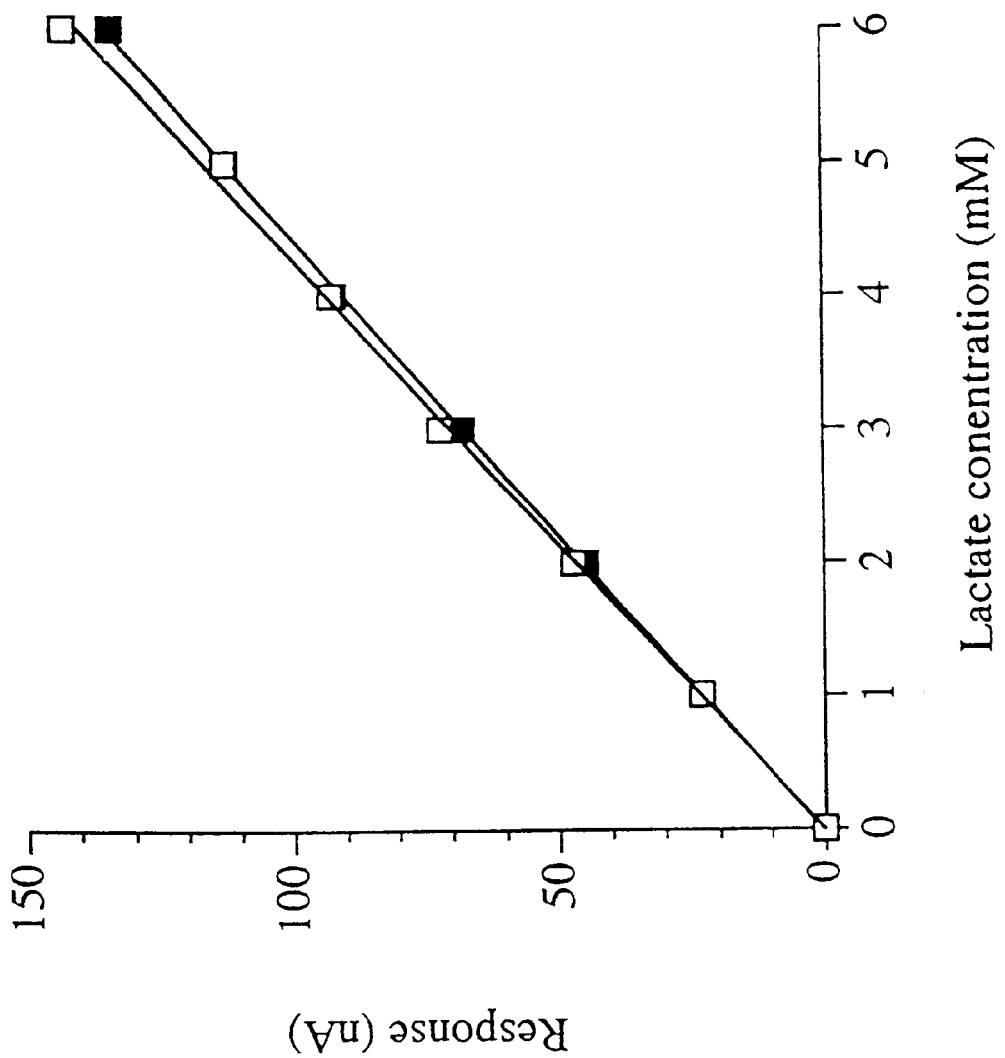

It can be seen from FIG. 3 that the calibration curves obtained before and after exposure to blood are virtually superimposable indicating that no significant biofouling of the sensor had occurred. This blood compatibility is unique and not seen with an electrode not previously exposed (preconditioned) in the sample. This is an extremely valuable characteristic of a sensor for clinical applications where electrode conditioning needs to be eliminated.

EXAMPLE 3

An enzyme electrode as described in Example 2 (incorporating a composite membrane comprised of layers (i), (ii) and (iii) was used for determining lactate concentrations in a range of whole blood samples. The electrode was exposed to each blood sample for approximately 10 minutes and washed with isotonic buffer solution in-between measurements. The results were compared with those obtained using a standard lactate analyser (Yellow Spring Instruments). A total of six samples were measured which gives an exposure time of at least one hour.

Figure 4:
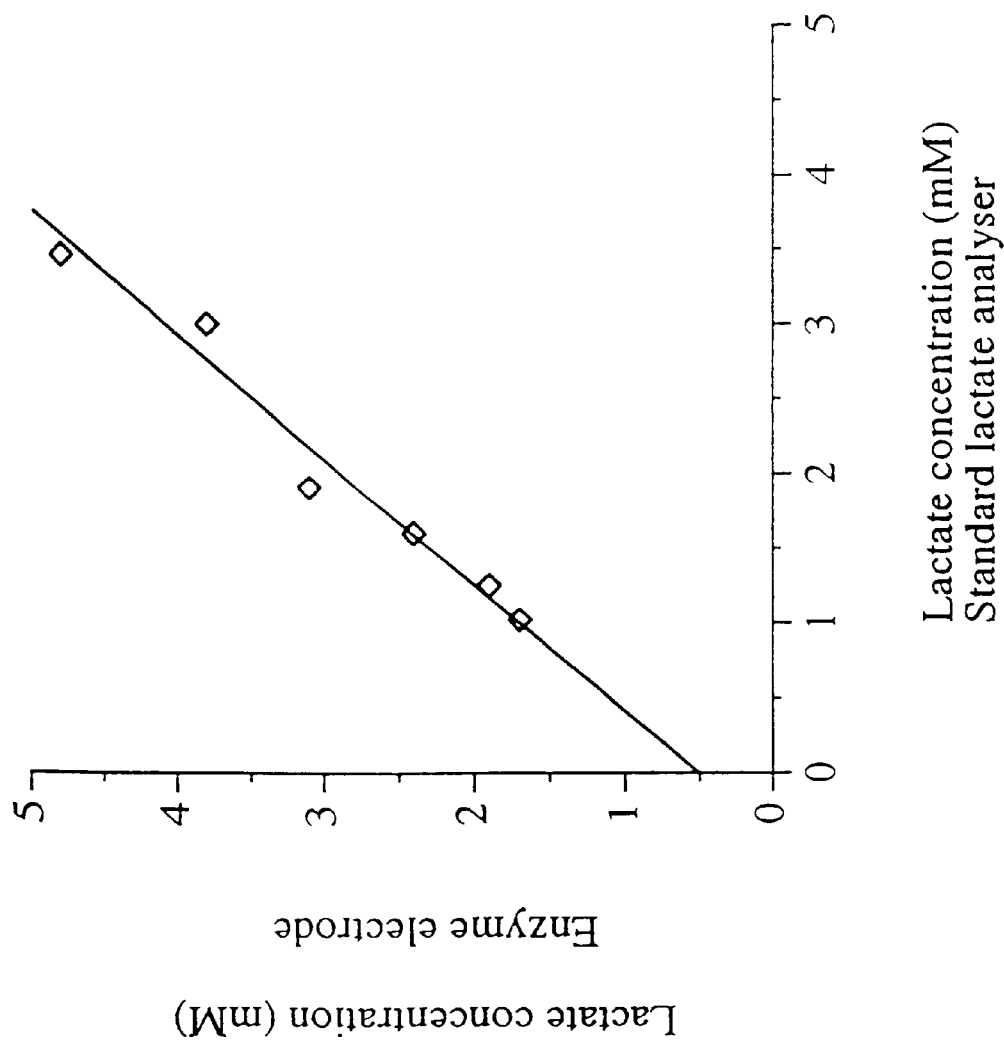

The results are plotted in FIG. 4. The enzyme electrode was found to give consistently higher readings but more importantly the two methods showed a good linear correlation. One important difference between the two methods which should be noted is that the blood sample is highly diluted before analysis in the standard analyser whereas the measurement with the enzyme electrode are carried out on undiluted whole blood. This difference should be taken into consideration when comparing the two methods.

EXAMPLE 4

A PVC membrane was produced by the following technique

An amount of 0.023 g of PLURONIC F-68 was dissolved in 7.5 ml of tetrahydrofuran (THF) and 0.5 g of PVC powder (molecular weight 200,000) was then added to the solution. The polymer was left to dissolve slowly overnight.

The solution was then placed on a Cuprophan dialysis membrane which was then spun at 1000 rpm for 90 seconds to produce a thin PVC membrane, the dialysis membrane functioning as a supporting matrix for the PVC layer.

A composite membrane of the type described in Example 2 was then produced save that the layer (i) was replaced by the PVC membrane produced in the present Example.

Figure 5:
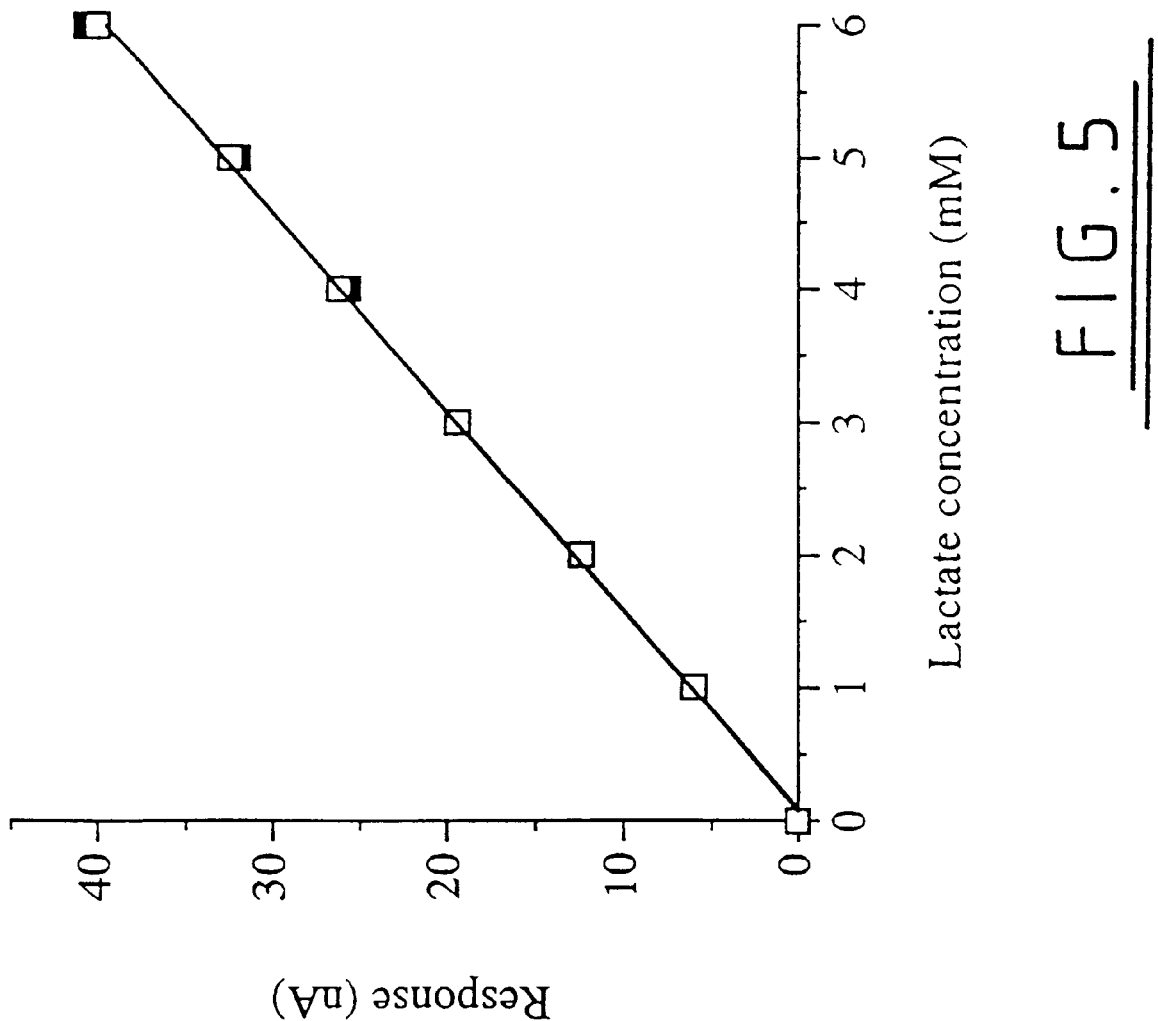

The composite membrane was then incorporated into a sensor of the type described above which was then calibrated both before exposure to whole blood and after the exposure to whole blood (total exposure at least 40 minutes) described in Example 5 below. The results are shown in FIG. 5 which shows calibration of the sensor before (□)y=6.664x−0.507, and after, (■)y=6.679x−0.607, exposure to blood. As can be seen from FIG. 5, the calibration curves before and after blood exposure are the same, clearly demonstrating that no biofouling had occurred.

EXAMPLE 5

An enzyme electrode as described in Example 4 was used for determining lactate concentrations in a total of eight whole blood samples. The electrode was exposed to each sample for approximately five minutes and washed with buffer solution in between measurements. The results were compared with those obtained using a standard lactate analyser (Yellow Spring Instruments).

Figure 6:
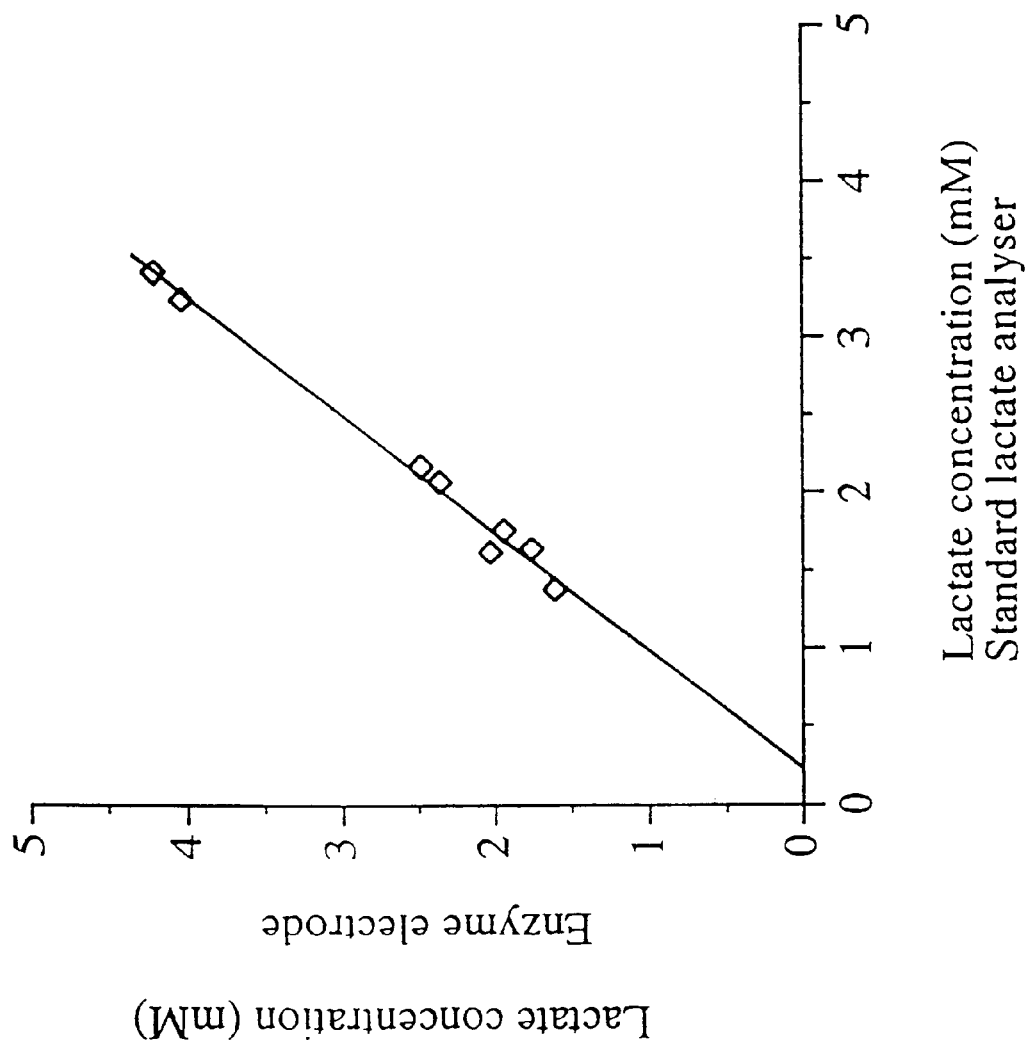
Figure 7A:
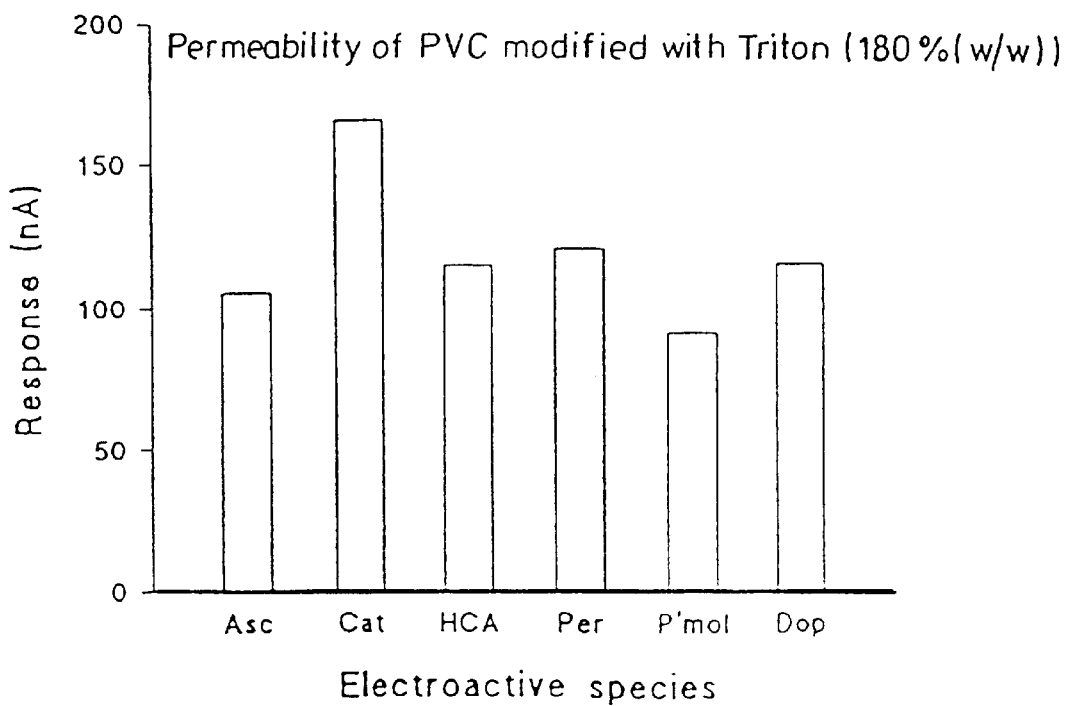
Figure 7B:
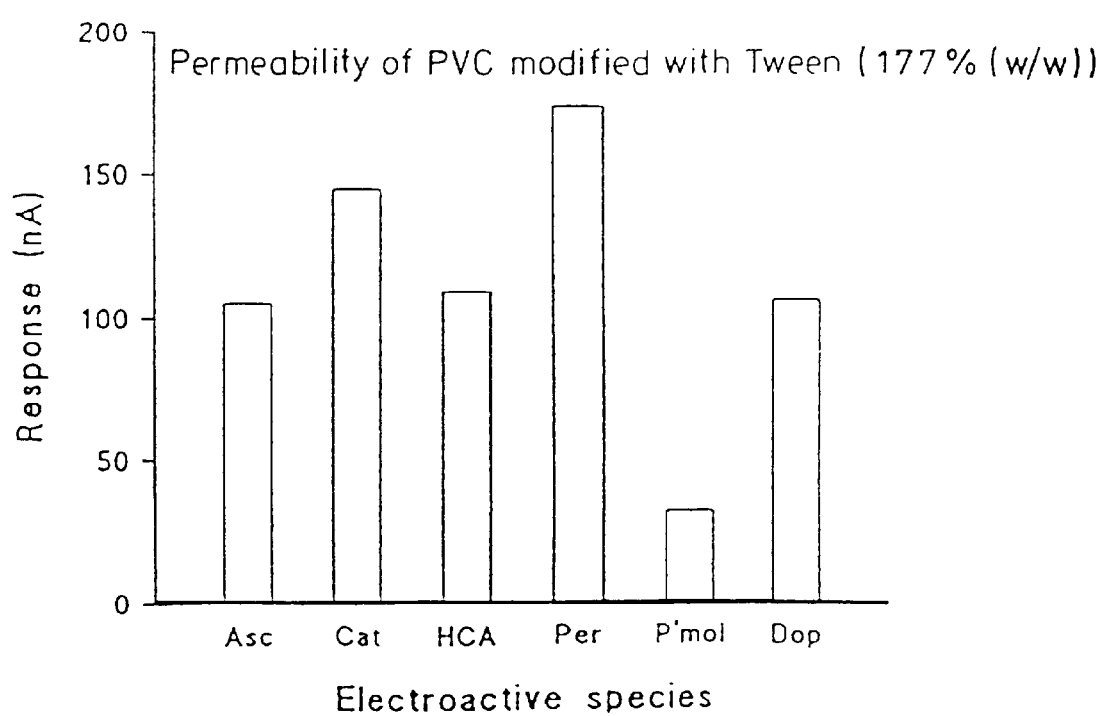
Figure 7C:
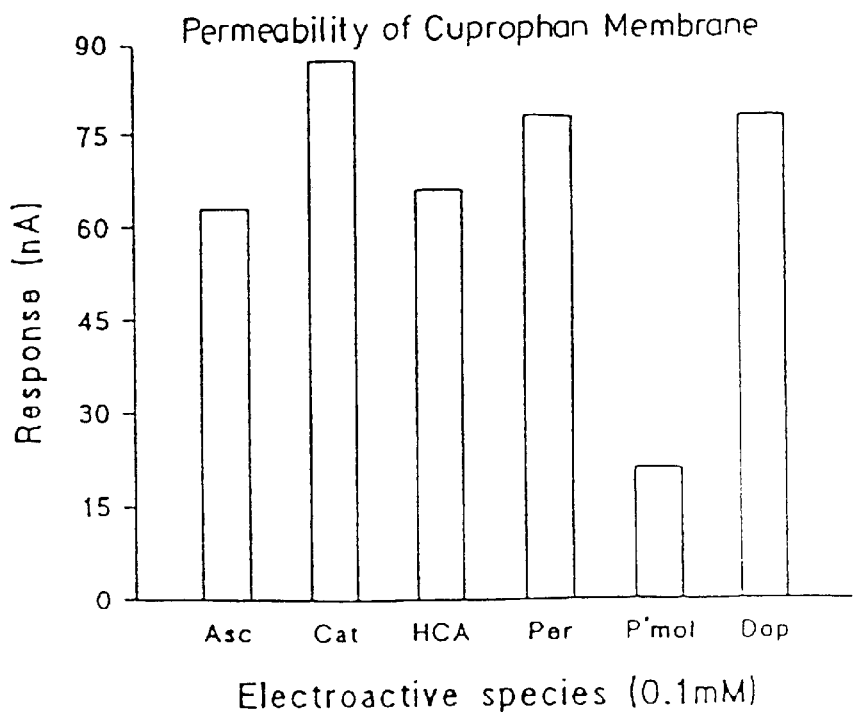
Figure 7D:
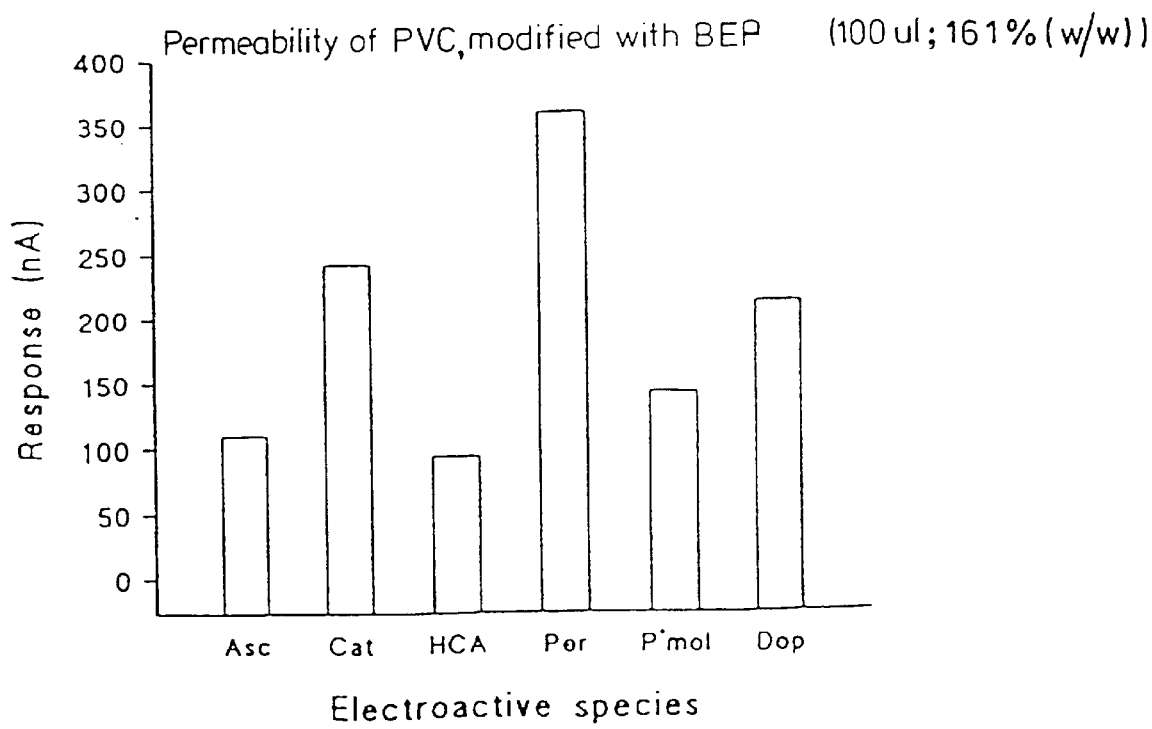

The results are plotted in FIG. 6. The enzyme electrode was found to give consistently higher readings but more importantly the two methods showed a good linear concentration. One important difference between the two methods which should be noted is that the blood sample is highly diluted before analysis in the standard analyser whereas the measurement with the enzyme electrode are carried out on whole blood. This difference should be taken into consideration when comparing the two methods.

EXAMPLE 6

PVC (0.06 g) was completely dissolved in tetrahydrofuran (5 ml). To the solution was then added surfactant (100 µl) to an amount indicated in FIG. 7. The resulting solution was then poured into a glass Petri dish (9 cm id), and the dish covered so as to effect slow evaporation of solvent (2 days). The resulting membranes were transparent, of even thickness and sufficiently robust to handle.

The membranes were evaluated using the following procedure.

The electrochemical cell, polarised and conditioned at +650 mV vs Ag/AgCl was covered with a Cuprophan membrane over which was layered a portion of the test membrane. The responses to a range of species (all at 100 uM concentration) were measured. These included acsorbate (Asc), catechol (Cat), hydrocaffeic acid (HCA), hydrogen peroxide (Per), paracetamol (P'mol) and dopamine (Dop), the results are shown in FIG. 7.

Figure 8:
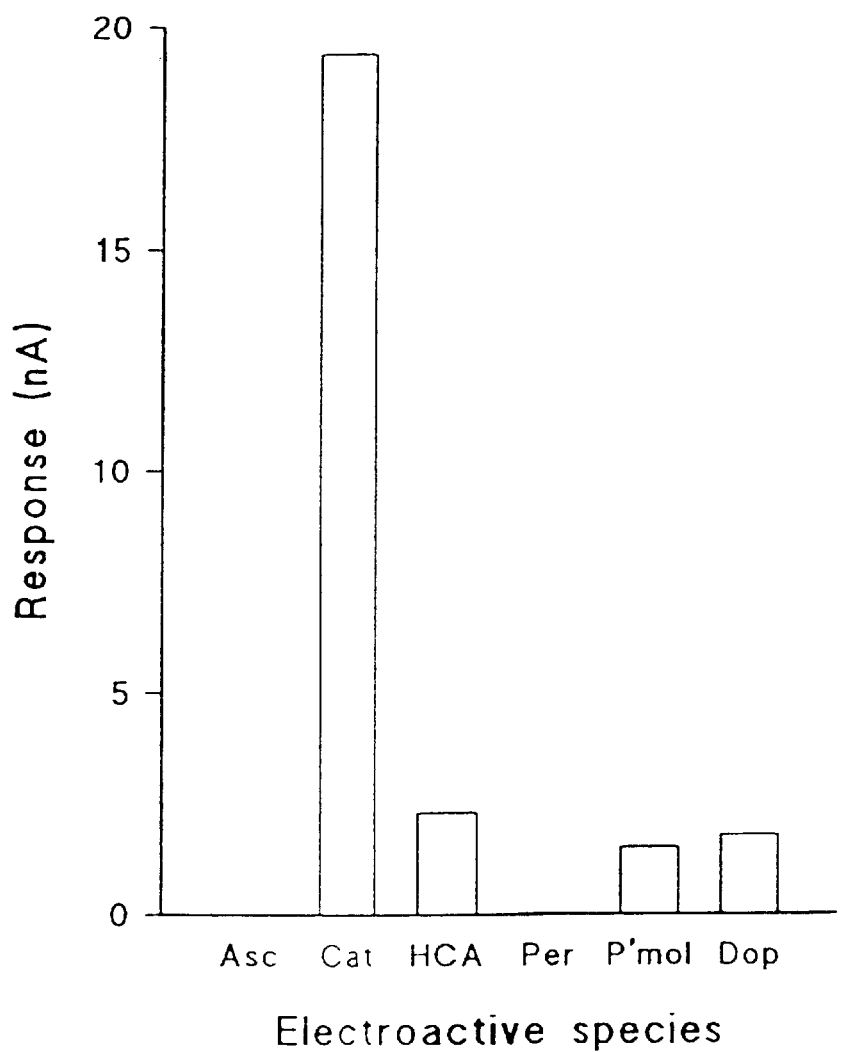

The surfactant modified membranes exhibit general high permeability properties mimicking and potentially exceeding those of the Cuprophan haemodialysis membrane in a phosphate buffer. This permeability is acceptable for haemodialysis and occurs regardless of pH buffer. However in a carboxylic acid based buffer (succinate buffer at acidic pH), the selectivity of PVC modified with BEP (FIG. 8) switches to that observed with PVC plasticised with isopropyl myristate (see WO-A-9216647) by rejecting polar hydrogen peroxide and ascorbate. This switching function of PVC modified with BEP would appear to have widespread applications—at blood acidity (pH 7.2) it may be used as a haemodialysing membrane in renal care applications; alternatively (at pH<3), it may be used as an outer membrane of an amperometric enzyme electrode for blood glucose measurement because of its reduced permeability.

EXAMPLE 7

As mentioned supra, it may be desirable that there be some continuous leakage of surfactant from membranes in accordance with the invention. This Example demonstrates surfactant loss from such membranes.

Figure 9:
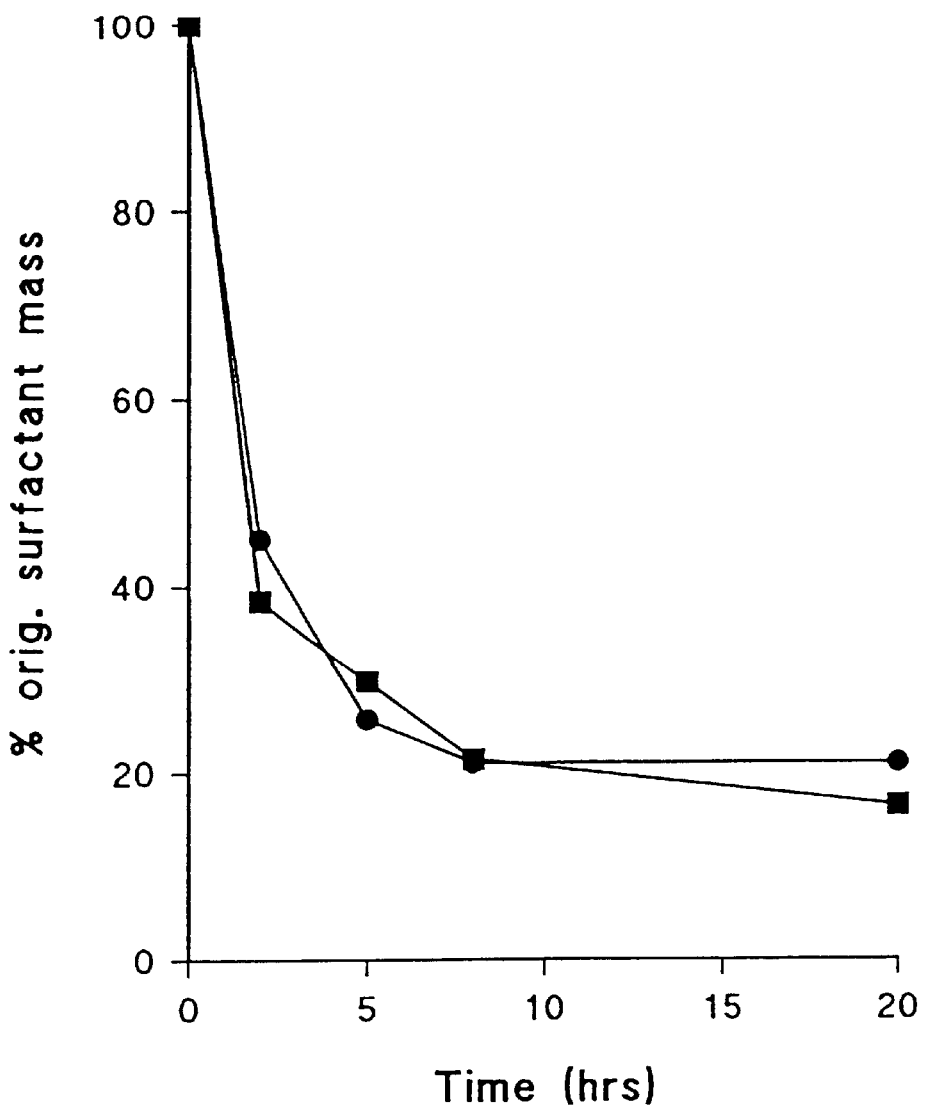

Membranes comprised of PVC and 2% v/v of either Tween 80 or TRITON X-100 were prepared by methods as described above. The resultant membranes were then bathed in distilled water and the weight loss of membranes measured at various times over a period of 12 hours. The results are shown in FIG. 9 which is self-explanatory. The surfactant loss has advantages in terms of providing a self-cleaning membranes.

EXAMPLE 8

A uniform PVC membrane of controlled thickness was fabricated by applying a solution of PVC (molecular weight 200,00) in THF containing 12% by weight (based on the weight of PVC) onto a highly permeable cuprophan dialysis membrane and using a spin coating technique to form a laminate structure comprised of the cuprophan membrane and PVC membrane, the latter containing 12% w/w PLURONIC F-68.

An enzyme electrode was constructed which comprised
(i) an enzyme layer comprised of lactate oxidase immobilised in a glutaraldehyde matrix,
(ii) a laminate as described as an outer membrane, and
(iii) a selective inner layer of SPEES/PES (prepared as in Example 2).

The enzyme electrode was provided in a flow through cell and tests were conducted as detailed below.

Figure 10:
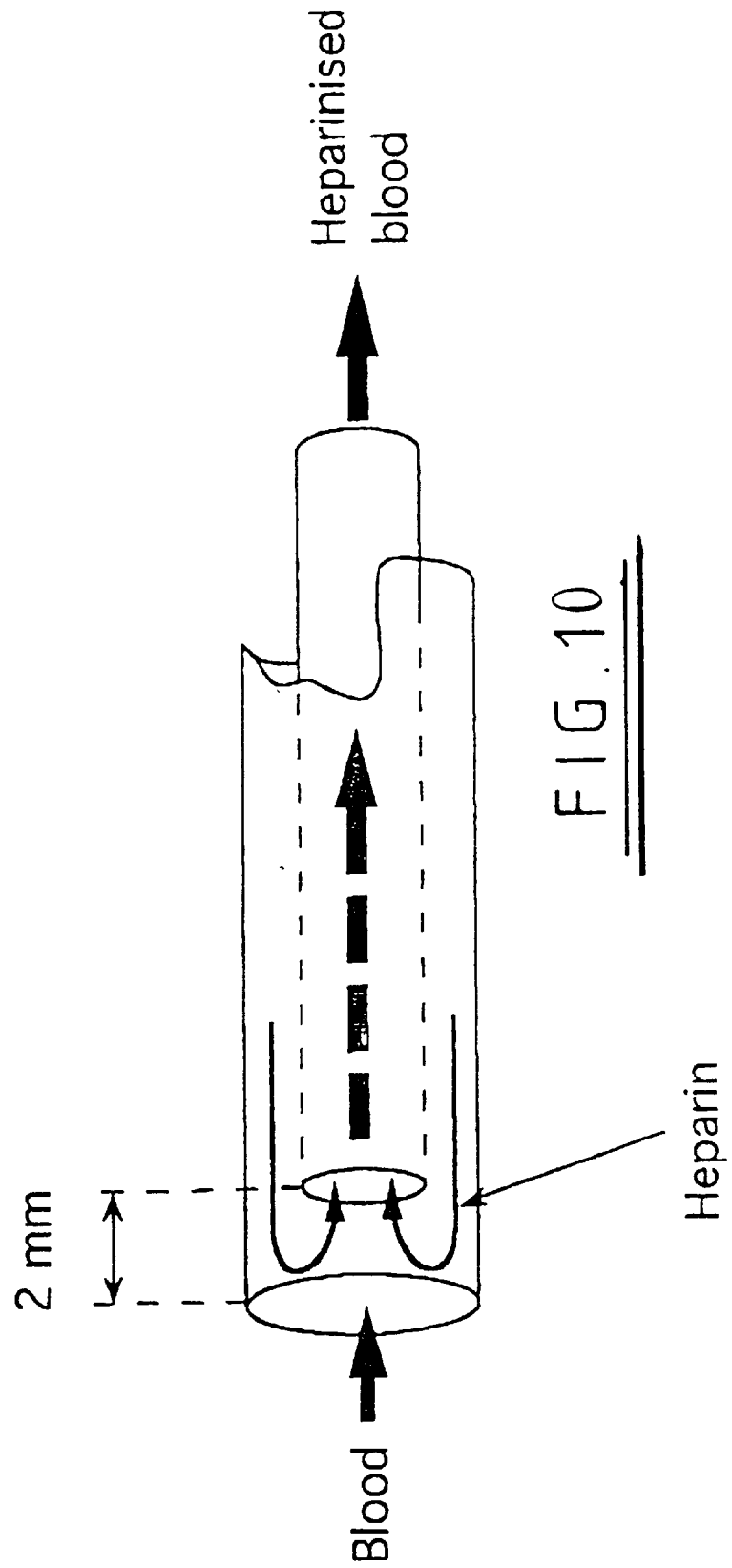

The electrodes were tested under continuous flow conditions using a double lumen catheter as illustrated in FIG. 10, which in certain tests was used to provide buffered lactate solution to the electrode and, in other tests, heparinised blood. For this latter purpose heparin flows in from right to left (as viewed in FIG. 10) along the outer lumen of the catheter. Blood is supplied to the left hand end of the catheter such that a mixture of heparin and blood is formed in, and flows from left to right through, the inner lumen of the catheter. The resulting heparinised blood is then supplied to the sensor.

Tests were conducted on whole blood admixed with heparin in a ratio of 3 parts by volume blood and 7 parts by volume heparin solution (200 IU $ml^{-1}$). The flow rate was 10 ml $h^{-1}$.

Figure 11A:
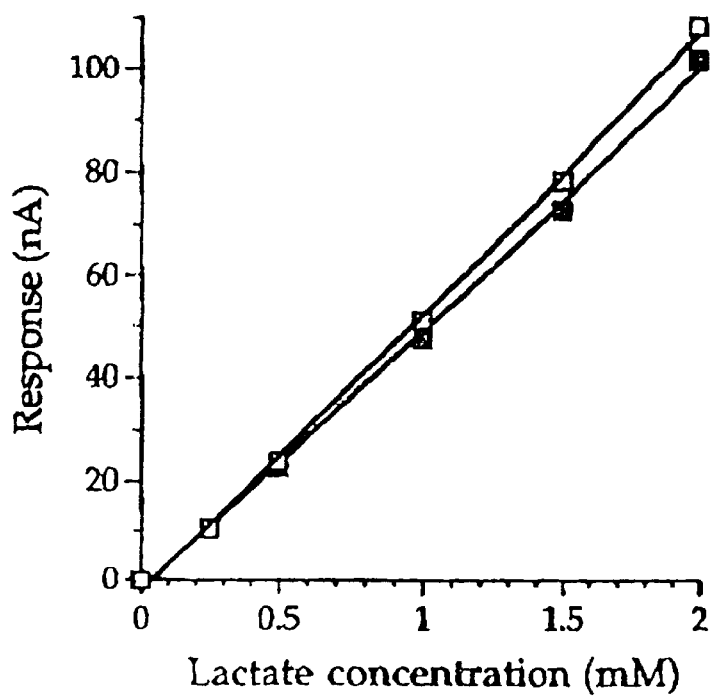

FIG. 11(a) illustrates results obtained for calibration of the flow-through lactate enzyme electrode before, ( ) y=54.366x−2.237, and after, (■) y=50.678x−1.743, monitoring of whole blood during a period of 3 h. It will be seen that the calibration remained substantially constant.

Figure 11B:
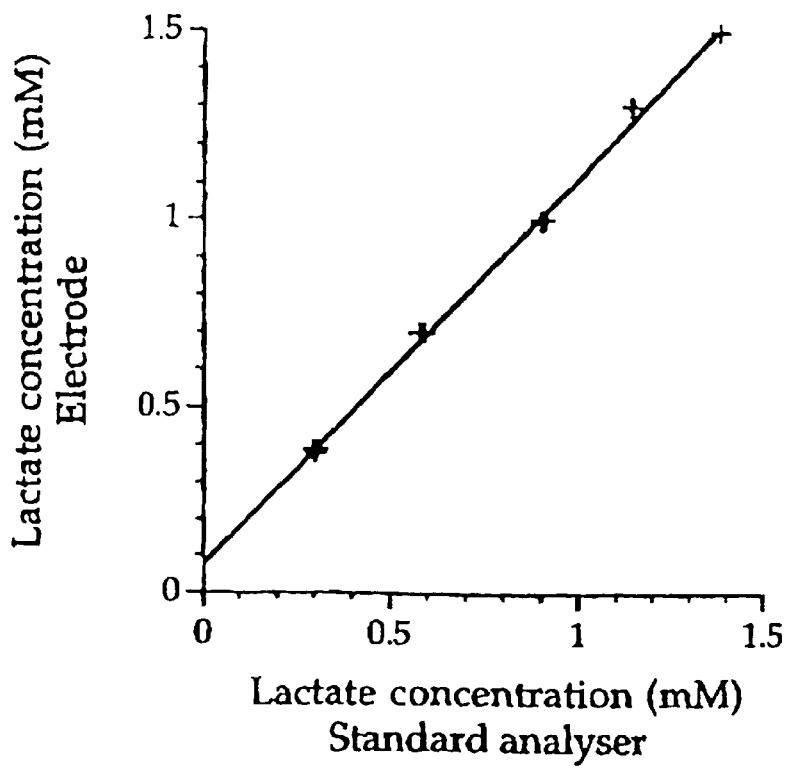

FIG. 11(b) illustrates correlation between blood lactate concentrations measured on-line with the enzyme electrode and off-line with a standard analyser: y=1.042x+0.078, $r^2$=0.998, n=9.

Figure 11C:
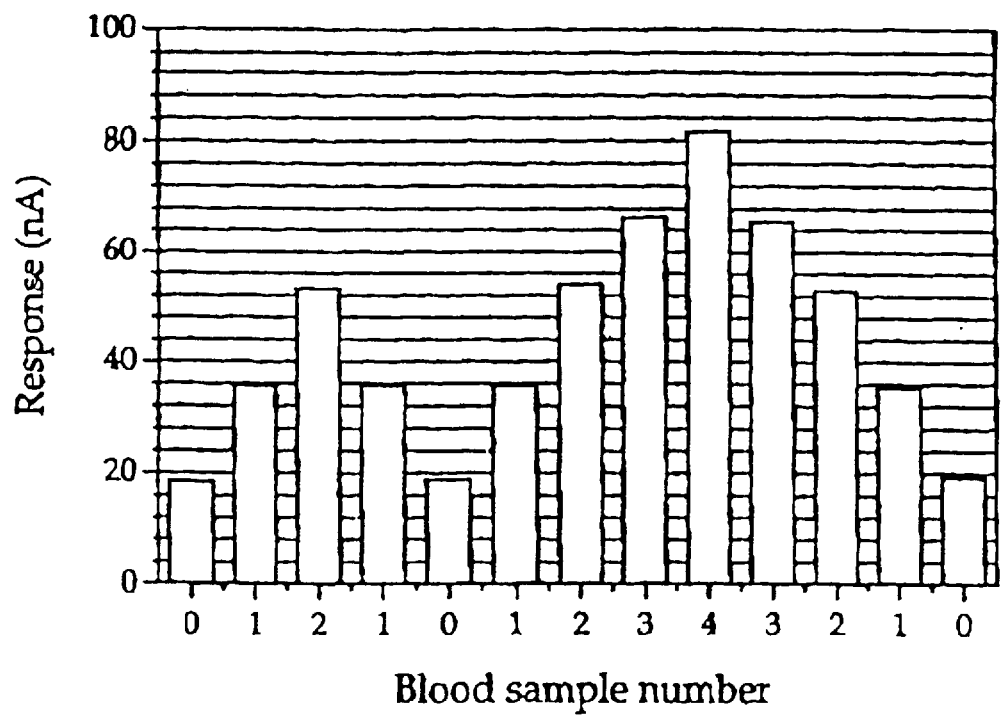

FIG. 11(c) illustrates induced step-changes of lactate in whole blood samples monitored on-line with lactate enzyme electrode; each plateau corresponding to the steady-state readings.

EXAMPLE 9

Laminates comprised of a cuprophan dialysis membrane and a PVC membrane were produced as described in Example 8 save for the amount of surfactant used.

For one laminate produced for this Example, the PVC (molecular weight 215,000 ex Scientific Polymer Products Inc.) incorporated 60% by weight (of the PVC) of Pluronic F-68. This laminate was used to construct an enzyme electrode of the type described in Example 8 but omitting the selective inner membrane.

A further laminate produced for this Example incorporated a membrane prepared from PVC (molecular weight 90,000 ex Fluka) containing 50% by weight of Pluronic F-68 and was used to construct an enzyme electrode of the type described in Example 8 (i.e. incorporating a SPEES-PES inner membrane).

Tests were conducted with these electrodes using a catheter of the type illustrated in FIG. 10 to produce a solution of 1 mM lactate in buffer solution (instead of heparinised blood). The buffer, pH 7.4, used for this and successive Examples comprised 0.0528 M $Na_2HPO_4$, 0.0156 M $NaH_2PO_4$. 0.051 M NaCl and 0.0016 M $K_2EDTA$.

Figure 12:
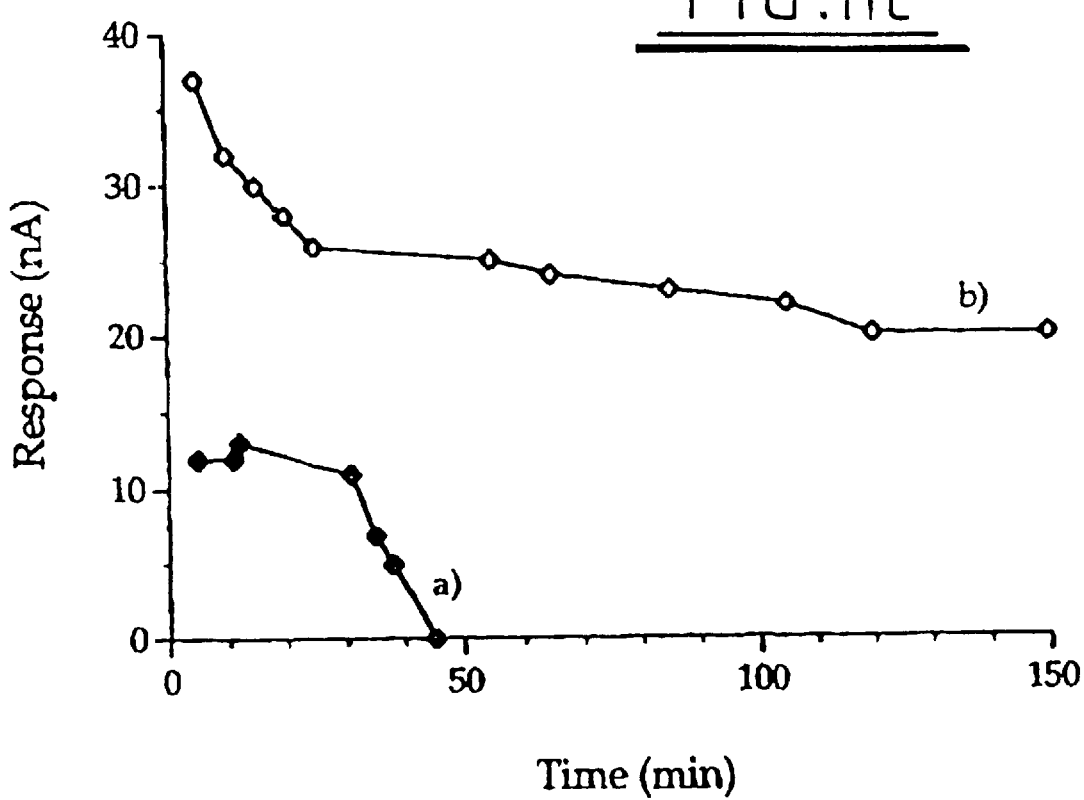

The results are shown in FIG. 12 in which (a) represents the electrode (♦) for which there was no selective inner membrane and the PVC contained 60% w/w PLURONIC F-68, and (b) represents (◇) for which there was a SPEES-PES inner membrane and the PVC contained 50% w/w PLURONIC F-68.

As seen from FIG. 12, both membranes were permeable to lactate but that depicted by line (a) was subject to surfactant leakage causing the membrane to lose permeability to the extent that response to lactate decreased rapidly and returned to baseline within 45 minutes. The membrane depicted by line (b) sowed satisfactory retention of surfactant.

EXAMPLE 10

An enzyme electrode was produced as disclosed in Example 8 save that
(i) the PVC (molecular weight 90,000) contained 50% by weight (of the PVC) of PLURONIC F-68, and
(ii) the enzyme layer incorporated two units of catalase.

A similar electrode was also produced but omitting the catalase.

Figure 13:
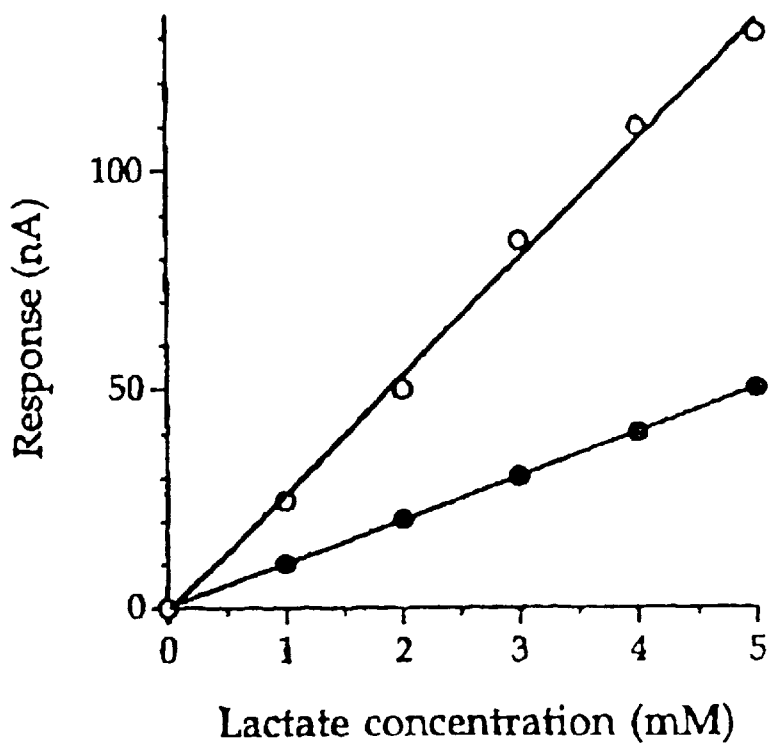

FIG. 13 illustrates the calibration of the flow through lactate enzyme electrodes combined with a double lumen catheter of the type illustrated in FIG. 10 using various concentrations of lactate dissolved in buffer. In FIG. 13. (●) represents the enzyme laminate with catalase and (○) represents laminate without catalase.

The membrane incorporating catalase provides a lower response which provides an accelerated dynamic response for the sensor through provision of a non-diffusive "sink" for some of the hydrogen peroxide produced.

EXAMPLE 11

A range of enzyme electrodes of the type described in Example 8 were produced save that the
(i) the PVC (molecular weight 90,000) incorporated 60% by weight (of the PVC) of PLURONIC F-68, and
(ii) the selective inner membrane was PTFE, PS or SPEES-PES.

The SPEES-PES membrane was produced as in Example 2. The PS (polysulphone) membrane was prepared from PS of molecular weight 50,000 (ex Aldrich) by dissolution of 2% w/v in THF, allowing the solution to stand overnight. Membranes were produced according to the previously described spin-coating procedure (Example 4). An applied volume of 100–800 ml of the 2% w/v polymer solution was used. The PTFE membrane was nr 4106 ex Universal Sensors Inc.

The enzyme electrodes were combined with a double lumen catheter of the type illustrated in FIG. 10 which was used to provide various concentrations of lactate dissolved in buffer to effect calibration.

Figure 14:
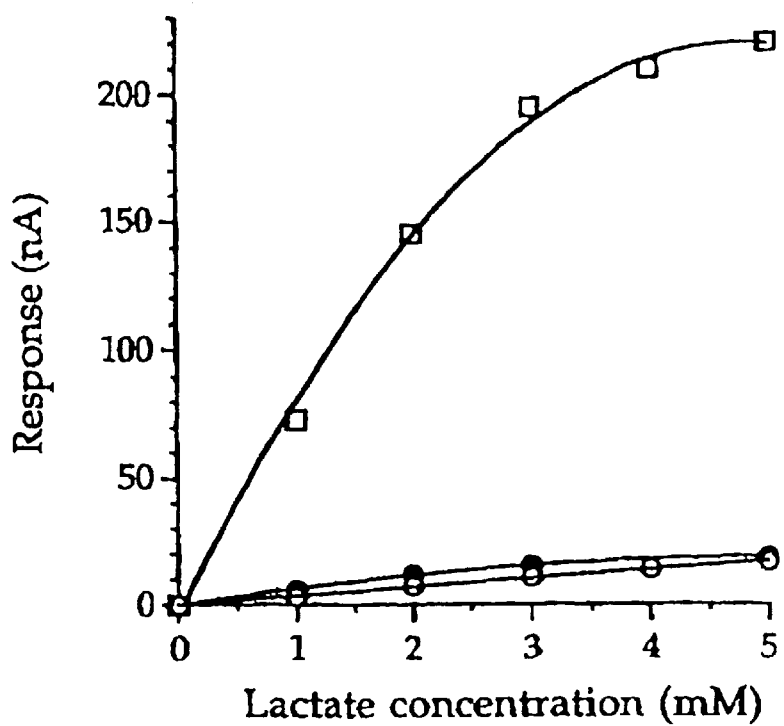

The results are shown in FIG. 14 in which (○) represents use of the PTFE inner membrane, (●) use of PES and (□) use of SPEES-PES.

The SPEES-PES was superior in terms of hydrogen peroxide permeability but PTFE was a good alternative since selectivity and response time were similar.

What is claimed is:

1. A membrane permeable by mass transport to uncharged species or to charged species of interest and comprising a synthetic polymeric material and a surface active agent which is miscible with the synthetic polymer, is distributed throughout the membrane and is present in an amount such as to provide for the permeability of the membrane to the species of interest; wherein continuous leakage of the surface active agent from the membrane provides a self-regenerating surface to minimize or reduce fouling of the surface.

2. A membrane as claimed in claim 1 wherein the synthetic polymeric material is poly(vinylchloride).

3. A membrane as claimed in claim 2 wherein the poly(vinylchloride) has a molecular weight (Mw) in the range 150,000 to 250,000.

4. A membrane as claimed in claim 3 wherein the poly(vinylchloride) has a molecular weight of about 200,000.

5. A membrane as claimed in claim 1 having a thickness of 0.1 to 200 microns.

6. A membrane as claimed in claim 1 wherein the surface active agent is a non-ionic surface active agent.

7. A membrane as claimed in claim 1 wherein the surface active agent is comprised of or incorporates polyoxyalkylene residues.

8. A membrane as claimed in claim 7 wherein the alkylene oxide is ethylene oxide and/or propylene oxide.

9. A membrane as claimed in claim 8 wherein the surface active agent is a compound of the formula (I)

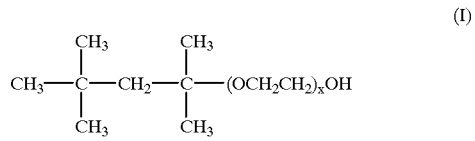

(I)

10. A membrane as claimed in claim 9 wherein the molecular weight of compound (I) is in the range 500 to 800.

11. A membrane as claimed in claim 10 wherein the molecular weight of compound (I) is in the range 600 to 700.

12. A membrane as claimed in claim 1 wherein the surface active agent comprises a block copolymer of ethylene oxide and propylene oxide.

13. A membrane as claimed in claim 12 wherein the block copolymer has a molecular weight of 5,000 to 10,000.

14. A membrane as claimed in claim 13 wherein the block copolymer has a molecular weight of 7,000 to 10,000.

15. A membrane as claimed in claim 1 wherein the surface active agent is L-α-phosphatidyl choline dipalmitoyl.

16. A membrane as claimed in claim 1 wherein the surface active agent is of the formula (II)

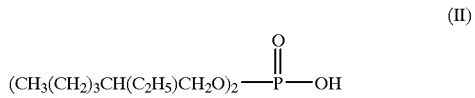

(II)

17. A membrane as claimed in claim 1 wherein the amount of surface active agent is less than 50% (w/w) of the synthetic polymer.

18. A membrane as claimed in claim 1 wherein the amount of surface active agent is at least 50% (w/w) of the synthetic polymer.

19. A membrane as claimed in claim 12 which comprises 6% to 100% of the surface active agent based on the weight of the synthetic polymer.

20. A membrane as claimed in claim 19 which comprises 40% to 70% of the surface active agent based on the weight of the synthetic polymer.

21. A membrane as claimed in claim 18 wherein the amount of the surface active agent is 150% to 200% (w/w) of the synthetic polymer.

22. A membrane structure comprising a membrane as claimed in claim 1 and a layer containing an immobilised enzyme.

23. A membrane structure as claimed in claim 22 wherein said layer comprises the enzyme cross-linked with bovine serum albumin in a glutararaldehyde matrix.

24. A membrane structure as claimed in claim 22 wherein the enzyme is an oxidase.

25. A membrane structure as claimed in claim 24 wherein the enzyme is lactate oxidase.

26. A membrane structure as claimed in claim 24 wherein the enzyme layer incorporates catalase.

27. A membrane structure as claimed in claim 22 wherein said layer incorporating the enzyme is provided between said membrane and a selective membrane for providing selectivity against interference.

28. A membrane structure as claimed in claim 27 wherein the selective membrane is comprised of a sulphonated poly(ether ether sulphone)/(poly (ether sulphone) polymer or cellulose acetate.

29. A sensor device comprising detecting means for detecting the amount of a species of interest in a sample and a membrane in accordance with claim 1 providing both a barrier function and a biocompatible interface function between the detecting means and the sample.

30. A sensor device as claimed in claim 29 wherein the detecting system comprises an electrochemical electrode system.

31. A sensor device as claimed in claim 30 wherein the electrochemical electrode system is of the non-potentiometric type.

32. A sensor device as claimed in claim 31 wherein the electrochemical electrode system comprises an amperometric electrode.

33. A sensor device as claimed in claim 29 which is a biosensor.

34. A sensor device as claimed in claim 29 which is a biosensor and which is provided with an enzyme on the electrode side of the membrane.

35. A sensor device as claimed in claim 34 wherein the enzyme is immobilised in a layer provided between the membrane and the electrode.

36. A sensor device as claimed in claim 35 wherein said layer comprises the enzyme cross-linked with bovine serum albumin in a glutararaldehyde matrix.

37. A sensor device as claimed in claim 34 wherein the enzyme is lactate oxidase.

38. A sensor device as claimed in claim 34 incorporating a further membrane between the enzyme and the electrode to provide selectivity against interferents.

39. A sensor device as claimed in claim 38 wherein the selective membrane is comprised of a sulphonated poly (ether ether sulphone)/(poly (ether sulphone) polymer or cellulose acetate.

40. A method of determining the amount of a selected component in a sample, the method comprising using a sensor device which incorporates means for detecting the amount of the component in a sample and a membrane as claimed in claim 22, said membrane or membrane structure being located in contact with the sample and providing both a barrier function and a biocompatible interface function between the sample and the detection means.

41. A method as claimed in claim 40 wherein the sample is whole blood and the selected component is lactate.

42. A method as claimed in claim 40 which is effected under continuous flow conditions.

43. A method of determining the amount of a selected component in a sample, the method comprising using a sensor device which incorporates means for detecting the amount of the component in a sample and a membrane as claimed in claim 1, said membrane or membrane structure being located in contact with the sample and providing both a barrier function and a biocompatible interface function between the sample and the detection means.

44. A membrane permeable by mass transport to uncharged species or to charged species of interest and comprising a synthetic polymeric material and a surface active agent which is miscible with the synthetic polymer, is distributed throughout the membrane and is present in an amount such as to provide for the permeability of the membrane to the species of interest; wherein continuous leakage of the surface active agent from the membrane provides a self-regenerating surface to minimize or reduce fouling of the surface, and wherein the membrane further comprises a reservoir of surface active agent to replenish that lost from the membrane.

* * * * *